April 14, 1942. H. C. SWIM Plant Pat. 508

ROSE PLANT

Filed Oct. 14, 1941

INVENTOR
H. C. Swim

By Robb & Robb
Attorneys.

Patented Apr. 14, 1942 Plant Pat. 508

UNITED STATES PATENT OFFICE

508

ROSE PLANT

Herbert C. Swim, Ontario, Calif., assignor to Armstrong Nurseries, Inc., Ontario, Calif., a corporation of California Application October 14, 1941, Serial No. 414,959

1 Claim. (Cl. 47—61)

The present discovery relates to a new and distinct variety of rose plant, originating as a bud sport of the rose "Golden Rapture" (American name for Geheimrat Duisberg).

This new rose was discovered by me growing upon its parent in the fields of Armstrong Nurseries, Inc., at Ontario, California, and its most clearly distinguishing feature is its vigorous growing habit, characterized by its strong canes, attaining a height of twelve to fourteen feet or more as distinguished from the usual height of three or four feet attained by the bush form of the rose "Golden Rapture."

The climbing habit above referred to is only one of its distinguishing features inasmuch as it also has a habit of producing many more flowers in the spring than are found at any one time on the bush parent variety, combined with the further habit of intermittent flowering during the rest of the season.

The flowers of this new rose variety are usually larger in size and greater in petalage than the flowers found on the bush "Golden Rapture," there being from seven to twelve petals and three to four petaloids more in the flowers of the new variety grown under the same conditions. No novelty of color of the bud or blossom is claimed.

The new variety has been asexually reproduced over an extended period of time, and these characteristics have proved to be permanently fixed through budding and grafting.

Figure 2:
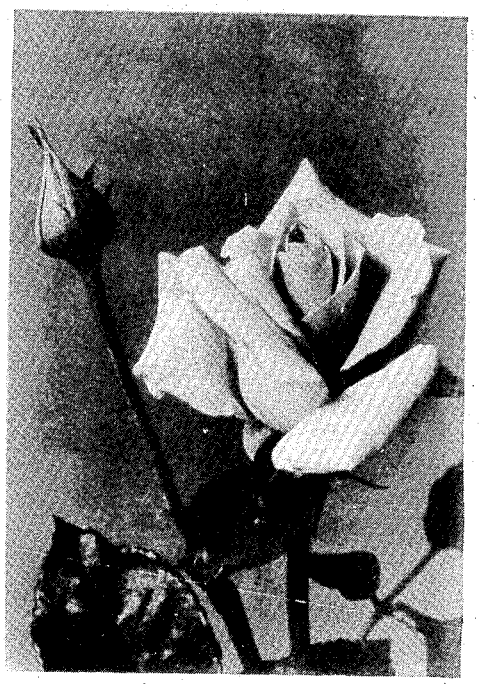
Figure 1:
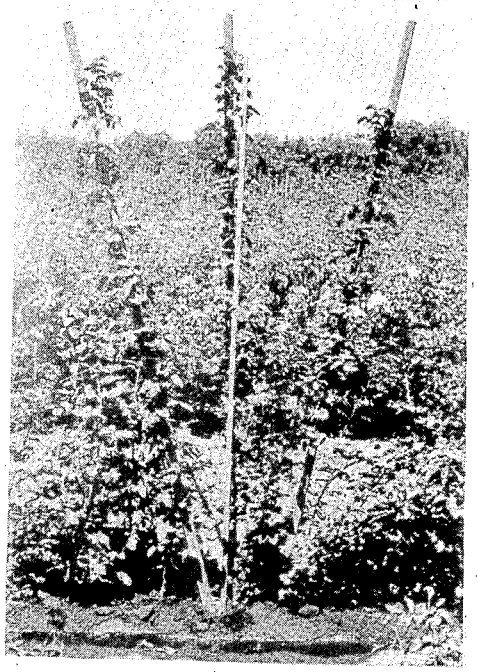

In the accompanying illustration, Figure 1 shows one year's growth of a specimen of this new variety of rose plant in association with a yardstick to graphically depict its vigorous climbing growth. Figure 2 shows a typical specimen of the flowers of this new variety.

The following is a detail description of the plant and flower of this new variety, all color terminology according with Ridgway's Color Standard:

Type: Half hardy; tall; climbing; outdoor; sport; for cut flowers and garden decoration.

Class: Climbing hybrid tea with Pernetiana also in ancestry.

Breeding or discovery: Sport.

*Parent.*—"Golden Rapture." Discovered as a limb sport on a plant in a row of bush "Golden Rapture" growing at a height so as to be easily discernible.

Propagation: Holds its distinguishing characteristics through succeeding propagations by grafting and budding.

*Flower*

Locality where grown: Ontario, California.

Flowers borne: Usually singly, sometimes several to stem; in irregular cluster; on strong, medium to long stems.

Quantity of bloom: Abundant; outdoors.

Continuity: One season to intermittent.

Fragrance: Combination of tea and spicy.

Bud:

*Pedicel.*—Medium length; medium heavy; erect; stiff; almost smooth; few gland-tipped cilia. *Color*—near Cosse Green, Plate V.

*Before calyx breaks.—Size*—medium. *Form*—long; pointed; with foliaceous appendages, some gland-tipped cilia, on the surface of the bud; with slender, much cut foliaceous parts extending beyond the tip of the bud equal to one-half to three-fourths or more of its length.

*As calyx breaks.*—Near Green Yellow, Plate V. Three sepals have both margins lined with stipitate glands. These three sepals also have much cut foliaceous parts. One sepal has one margin lined with stipitate glands and one margin lined with woolly tomentum. The other sepal has both margins lined with woolly tomentum.

*As first petal opens.—Size*—medium. *Form*—ovoid. *Color*: outside—near Lemon Chrome, Plate IV, at base and maintaining near Lemon Chrome with shadings of near Empire Yellow, Plate IV, to tip of petal. Empire Yellow usually quite prominent at tip end of petal. Inside—entire petal quite uniformly near Lemon Chrome, Plate IV. *Opening*—opens up well.

Bloom:

*Size.*—When fully open—medium; 3⅛ inches to 4¼ inches.

*Petalage.*—Semi-double; 15 to 20 petals; arranged regularly, sometimes with numerous petaloids forming a cushion in center.

*Form.*—High center, at first; becoming open; petals remaining at first tightly rolled outward; at maturity, tightly rolled outward.

Petals: Thick; leathery; with inside velvety and outside satiny.

*Shape.*—Outside—varies from broadly obovate to orbicular. Most of the outside petals are scalloped with one or more notches. However, some have no notches. Notches of one outside petal are not usually similar to those of any other outside petal. Intermediate—broadly obovate but occasionally irregular. Usually smooth around the edge of petal, but sometimes scalloped with one or more notches. Inside—usually obovate. Sometimes irregular and usually scalloped with one or more notches. Petaloids when present are very irregular and are much scalloped and notched.

*Color.*—Colors may be modified by being shaded and washed with other colors.

This description of a newly opened flower was made from a rose grown outdoors in the month of August, 1941, at Ontario, California.

*Color.*—Outside petal (other than first petal to open): outside surface—near Lemon Chrome, Plate IV, at base, blending gradually to near Amber Yellow, Plate XVI, with shadings of Empire Yellow, Plate IV. Sometimes tip of petal is mottled with near Straw Yellow, Plate XVI. Outside petal (other than first petal to open): inside surface—near Lemon Chrome, Plate IV, with shadings of Empire Yellow, Plate IV. Tip of petal sometimes mottled with near Straw Yellow, Plate XVI. Intermediate petal: outside surface—point of attachment near Wax Yellow, Plate XVI, blending abruptly to near Amber Yellow, Plate XVI. Entire petal, with exception of point of attachment, usually quite uniformly near Amber Yellow, Plate XVI. Inside surface—point of attachment near Lemon Chrome, Plate IV, shaded near Empire Yellow, Plate IV, blending very gradually to near Amber Yellow, Plate XVI, at tip of petal. Inner petal: outside surface—point of attachment near Wax Yellow, Plate XVI, blending abruptly to near Amber Yellow, Plate XVI. Entire petal, with exception of point of attachment, usually quite uniformly near Amber Yellow, Plate XVI. Inside surface—point of attachment near Lemon Chrome, Plate IV, shaded near Empire Yellow, Plate IV, blending very gradually to near Amber Yellow, Plate XVI, at tip of petal.

This description was made from a rose that was open for three days indoors, in the month of August, 1941, at Ontario, California:

Outside petal: outside surface—point nearest attachment near Lemon Chrome, Plate IV, quickly shading to near Pinard Yellow, Plate IV, which in turn quickly washes or blends into Sea Foam Yellow, Plate XXXI. Near Sea Foam Yellow is present from the tip of the petal to ¾, more or less, of the entire length of the petal. Inside surface—point nearest attachment near Lemon Chrome, Plate IV, blending quickly to near Sea Foam Yellow, Plate XXXI. Near Sea Foam Yellow is present from the tip of the petal to ¾, more or less, the entire length of the petal. Inside petal: outside surface—point of attachment near Lemon Chrome, Plate IV, blending abruptly to near Pinard Yellow, Plate IV, which in turn blends very gradually into Sea Foam Yellow, Plate XXXI. The near Sea Foam Yellow is present for ¾, more or less, the distance from the tip to the base of the petal. Inside surface—point of attachment near Lemon Chrome, Plate IV, blending very gradually into near Sea Foam Yellow, Plate XXXI. The near Sea Foam Yellow is present for ½, more or less, the distance from the tip to the base of the petal.

*General color effect.*—Newly opened flower—near Empire Yellow, Plate IV, predominating; washing or blending to near Amber Yellow, Plate XVI, at side margin. Where petals roll outward at tip color varies from near Amber Yellow, Plate XVI, to near Straw Yellow, Plate XVI. Three days open—near Sea Foam Yellow, Plate XXXI, predominating, but blending gradually to near Pinard Yellow, Plate IV, at the base of each petal.

*Behavior.*—Drop off cleanly; affected by hot, dry weather as follows: decrease some in size and fade lighter more quickly.

*Flower longevity.*—On bush in garden, 3 to 4 days in August, 1941; cut roses grown outdoors kept at living room temperatures, 4 days in August, 1941.

*Reproductive organs*

Stamens: Many; arranged more or less irregularly; mixed with petaloids.

Filaments: Short to medium; near Lemon Chrome, Plate IV, blending very gradually to near Lemon Yellow, Plate IV, at point of attachment to anther. Lemon Chrome predominating; most with anthers.

Anthers: Medium to large; open at various times; both sides near Pinard Yellow, Plate IV, and both sides heavily margined with near Cadmium Yellow, Plate III.

Pollen: Moderately abundant; near Cadmium Yellow, Plate III.

Pistils: Medium number.

Styles: Uneven; medium length; medium heavy; loosely bunched; near pale Viridine Yellow, Plate V, blending abruptly to near Spectrum Red, Plate I, at base of stigma.

Stigma: Between near Buff Yellow, Plate IV, and near Apricot Yellow, Plate IV.

Ovaries: Some protruding from calyx.

Hips: Almost mature hips medium sized, short, depresso-globose with inconspicuous neck. Walls moderately thick, moderately rough. When mature between near Russet, Plate XV, and near Cinnamon Brown, Plate XV.

Sepals: Permanent; moderately long; recurved.

*Color.*—Inside (this description applies to sepal of freshly opened flower)—some sepals near Cosse Green, Plate V, covered by woolly tomentum. Other sepals near Cosse Green, Plate V, covered by woolly tomentum with near Greenish Yellow, Plate V, markings and blendings along a portion of each margin. The three sepals having foliaceous parts are usually near Cress Green, Plate XXXI, at tip, blending gradually to near Lettuce Green, Plate V, at point of attachment. These shadings and blendings also covered with woolly tomentum. Outside (this description applies to sepal of freshly opened flower)—between near Lettuce Green, Plate V, and near Cosse Green, Plate V, at base blending gradually to near Cress Green, Plate XXXI, at tip.

Seeds: Many; medium to large.

*Plant*

Foliage:

*Leaves.*—Pinnately compound of 3 to 5 leaflets; moderately abundant; medium to large; leathery; semi-glossy.

*Leaflets.*—Broadly ovate with apex acute; base obtuse to round; margin simply serrate.

*Color.*—Mature: Upper surface—near Yew Green, Plate XXXI; under surface—near Aspodel Green, Plate XLI, veined Light Cress Green, Plate XXXI. Young: upper surface—near Cress Green, Plate XXXI, margined with near Anthracene Purple, Plate XLIV. Sometimes near Anthracene Purple blends gradually into the near Cress Green and sometimes the Anthracene Purple forms a distinct narrow margin. In most cases, the mid-rib blends gradually along a very slender line from near Anthracene Purple at the base to near Cress Green as it nears the apex; under surface—near Light Cress Green, Plate XXXI, with very narrow hair line margin of near Neutral Red, Plate XXXVIII, with shadings or blendings of near Neutral Red which are sometimes very prominent but sometimes very lightly shaded.

*Rachis.*—Medium heavy. Upper side—grooved; sparsely hairy in groove with stipitate glands moderately numerous on margins of groove. Under side—moderately smooth with few small prickles.

*Stipules.*—Medium long; medium wide; with medium long points, turning out at an angle of more or less than 45°.

*Disease.*—Resistant to mildew.

Growth:

*Habit.*—Climbing; much branched.

*Growth.*—Vigorous.

*Canes.*—Moderately heavy.

*Main stems.*—Near Rainette Green, Plate XXXI. Side exposed to most sun has shadings of near Kronberg's Green, Plate XXXI. *Large prickles*—several to many; medium straight; some hooked downward; some declining; with narrow base; varying from near Carob Brown, Plate XIV, to irregular blending of Carob Brown to near Russet, Plate XV. There is a marked difference in the color of prickles on different stems. *Small prickles*—few; near Carob Brown, Plate XIV, sometimes blending to near Russet, Plate XV. *Hairs*—no hairs visible to the naked eye. Under strong magnifying glass a fuzzy bloom may be seen.

*Branches.*—Near Light Elm Green, Plate XVII. Side exposed to most sun near Light Cress Green, Plate XXXI. *Large prickles*—several to many; medium length; some hooked downward; some declining upward; with short, narrow base. There is a marked difference in the color of prickles on different branches, also a marked difference in the color of prickles on the same branch. Some prickles are near Citron Green, Plate XXXI, at base and tip blending gradually to a near Chrysolite Green, Plate XXXI, at center section. Others have near Chrysolite Green, Plate XXXI, from tip to center blending into near Russet-Vinaceous, Plate XXXIX, at base. Others are near Citron Green, Plate XXXI, with a distinct margin of near Pompeian Red, Plate XIII, around the base of prickle. Others are near Medal Bronze, Plate IV, blending to near Dark Olive Buff, Plate XL. In fact, there are many variations of the above color descriptions. *Small prickles*—few; vary also, depending on what branch and what part of that branch they happen to be on. They are similar in color and shadings to the larger prickles on that portion of the branch they happen to be on. *Hairs*—apparently no hairs visible to the naked eye. Under strong magnifying glass a few and sometimes no hairs are visible, but a very fine fuzzy bloom may be seen.

*New Shoots.*—Near Absinthe Green, Plate XXXI, blending to near Rainette Green, Plate XXXI, sometimes shaded with near Yellowish Oil Green, Plate V. Side exposed to most sun has blendings of near Biscay Green, Plate XVII, and near Yellowish Oil Green, Plate V, with faint shadings of near Neutral Red, Plate XXXVIII, toward tip of shoot. *Large prickles*—several to many; medium length; hooked downward; some declining upward; round base; near Van Dyke Red, Plate XIII, at base blending gradually to near deep Sea Foam Green, Plate XXXI, at point on tip. *Small prickles*—few; near Van Dyke Red, Plate XIII, at base blending gradually to near deep Sea Foam Green, Plate XXXI, at point on tip. *Hairs*—apparently no hairs, but under a strong magnifying glass a fuzzy bloom may be seen.

I claim:

A new and distinct variety of rose plant, characterized as to novelty by its vigorous climbing habit of growth, its increased floriferousness and remontant habit in comparison with its parent, and the large size and increased petalage flowers, substantially as shown and described.

HERBERT C. SWIM.